(12) United States Patent
Gallagher et al.

(10) Patent No.: US 7,507,341 B2
(45) Date of Patent: *Mar. 24, 2009

(54) METHOD OF AND APPARATUS FOR CONVERTING BIOLOGICAL MATERIALS INTO ENERGY RESOURCES

(75) Inventors: Michael T. Gallagher, Highland Park, IL (US); Jeffrey Held, Chicago, IL (US); Satya P. Chauhan, Columbus, OH (US); Anthony J. Tomasello, Libertyville, IL (US)

(73) Assignee: Opencel LLC, Glencoe, IL (US)

( * ) Notice: Subject to any disclaimer, the term of this patent is extended or adjusted under 35 U.S.C. 154(b) by 329 days.

This patent is subject to a terminal disclaimer.

(21) Appl. No.: 11/198,703

(22) Filed: Aug. 5, 2005

(65) Prior Publication Data

US 2006/0118485 A1    Jun. 8, 2006

Related U.S. Application Data

(63) Continuation-in-part of application No. 10/795,944, filed on Mar. 8, 2004, now Pat. No. 7,001,520, which is a continuation of application No. 10/270,420, filed on Oct. 15, 2002, now Pat. No. 6,709,594, which is a continuation-in-part of application No. 10/107,614, filed on Mar. 26, 2002, now Pat. No. 6,540,919, which is a continuation of application No. 09/612,776, filed on Jul. 10, 2000, now Pat. No. 6,395,176, which is a continuation-in-part of application No. 09/468,427, filed on Dec. 21, 1999, now abandoned, which is a continuation of application No. 09/229,279, filed on Jan. 13, 1999, now Pat. No. 6,030,538.

(60) Provisional application No. 60/599,355, filed on Aug. 6, 2004.

(51) Int. Cl.
*C02F 3/28* (2006.01)

(52) U.S. Cl. .................... 210/603; 48/127.3; 48/197 A; 205/637; 205/688; 205/751; 210/609; 210/748

(58) Field of Classification Search ................. 210/748
See application file for complete search history.

(56) References Cited

U.S. PATENT DOCUMENTS 980,463 A    1/1911    Welcome (Continued)

FOREIGN PATENT DOCUMENTS

DE    4 101 076    8/1991

(Continued)

OTHER PUBLICATIONS

Bradley et al., *Bipolar Electrodeposition on Nanotubes* (USA).

(Continued)

*Primary Examiner*—Peter A Hruskoci
(74) *Attorney, Agent, or Firm*—Marshall, Gerstein & Borun LLP

(57) ABSTRACT

A method of converting biological material into energy resources includes transmitting biological material to a pulsed electric field (PEF) station, and applying a PEF to the biological material within a treatment zone in the PEF station to generate treated biological material. The method also includes transmitting the treated biological material to a biogenerator, and processing the treated biological material in the biogenerator to produce an energy resource. A converter may carry out this process, and may include the PEF station and the biogenerator.

6 Claims, 8 Drawing Sheets

U.S. PATENT DOCUMENTS

| | | | |
|---|---|---|---|
| 3,265,605 | A | 8/1966 | Doevenspeck |
| 3,280,982 | A | 10/1966 | Barto |
| 3,397,140 | A | 8/1968 | Dea |
| 3,670,891 | A | 6/1972 | Allen |
| 3,699,906 | A | 10/1972 | Gallo |
| 3,913,500 | A | 10/1975 | Paccione et al. |
| 3,962,069 | A | 6/1976 | Inoue et al. |
| 4,013,552 | A | 3/1977 | Kreuter |
| 4,043,047 | A | 8/1977 | Galliker |
| 4,101,400 | A | 7/1978 | Pepping |
| 4,193,206 | A | 3/1980 | Maffet |
| 4,306,978 | A | 12/1981 | Wurtz |
| 4,367,132 | A | 1/1983 | Bell et al. |
| 4,561,953 | A | 12/1985 | Muralidhara et al. |
| 4,592,291 | A | 6/1986 | Sullivan, III |
| 4,608,179 | A | 8/1986 | Deal |
| 4,620,493 | A | 11/1986 | Carlson |
| 4,631,133 | A | 12/1986 | Axelrod |
| 4,655,932 | A | 4/1987 | Roslonski |
| 4,671,874 | A | 6/1987 | Fremont et al. |
| 4,747,920 | A | 5/1988 | Muralidhara et al. |
| 4,755,305 | A | 7/1988 | Fremont et al. |
| 4,861,496 | A | 8/1989 | Diaz |
| 4,917,785 | A | 4/1990 | Juvan |
| 4,957,606 | A | 9/1990 | Juvan |
| 4,971,705 | A | 11/1990 | Roslonski |
| 5,026,484 | A | 6/1991 | Juvan |
| 5,034,111 | A | 7/1991 | Kondo et al. |
| 5,037,524 | A | 8/1991 | Juvan |
| 5,037,560 | A | 8/1991 | Gayman |
| 5,048,404 | A | 9/1991 | Bushnell et al. |
| 5,049,248 | A | 9/1991 | Muralidhara et al. |
| 5,091,079 | A | 2/1992 | Gayman |
| 5,143,626 | A | 9/1992 | Nugent |
| 5,230,809 | A | 7/1993 | Roslonski |
| 5,326,530 | A | 7/1994 | Bridges |
| 5,464,513 | A | 11/1995 | Goriachev |
| 5,507,927 | A | 4/1996 | Emery |
| 5,522,553 | A | 6/1996 | LeClair et al. |
| 5,630,915 | A | 5/1997 | Greene et al. |
| 5,690,978 | A | 11/1997 | Yin et al. |
| 5,695,650 | A | 12/1997 | Held |
| 5,801,489 | A | 9/1998 | Chism, Jr. et al. |
| 5,846,425 | A | 12/1998 | Whiteman |
| 5,893,979 | A | 4/1999 | Held |
| 5,965,093 | A | 10/1999 | Adams |
| 5,976,719 | A * | 11/1999 | Kim et al. ............... 429/2 |
| 6,030,538 | A | 2/2000 | Held |
| 6,090,266 | A * | 7/2000 | Roychowdhury ........... 205/637 |
| 6,395,176 | B1 | 5/2002 | Held et al. |
| 6,402,065 | B1 | 6/2002 | Higgins |
| 6,491,820 | B2 | 12/2002 | Held et al. |
| 6,540,919 | B2 | 4/2003 | Held et al. |
| 6,709,594 | B2 | 3/2004 | Held et al. |
| 6,984,305 | B2 * | 1/2006 | McAlister ............... 205/637 |

FOREIGN PATENT DOCUMENTS

| | | |
|---|---|---|
| FR | 2327965 | 6/1977 |
| JP | 53-91468 | 11/1978 |
| JP | 60-25597 | 8/1985 |
| JP | 1-210100 | 8/1989 |
| JP | 1-307500 | 12/1989 |
| JP | 10-137778 | 5/1998 |
| JP | 11-179391 | 7/1999 |
| JP | 11-253999 | 9/1999 |
| JP | 2000-185238 | 7/2000 |
| WO | WO 98/58740 | 12/1998 |
| WO | WO 99/24372 | 5/1999 |
| WO | WO 02/04356 | 1/2001 |
| WO | WO 2004/004036 | 1/2004 |

OTHER PUBLICATIONS

Castro et al., *Microbial Inactivation of Foods by Pulsed Electric Fields*, J. Food Proc. Pres. 17:47-73 (1993) (USA).
Chauhan, S., *Feasability of Biosludge Dewatering Using Pulsed Electric Fields*, Battelle Final Report, 1-24 (1998).
*Consideration of Sludge Dewatering Methods* in The Microbiology of Waste Waters (W.B. Sauders & Co.) pp. 6-8, 17 (1971) (USA).
*Controlling Fluid Flow with Porous Metals*, Machine Design (Jan. 8, 1987).
Cox et al., Review of Recent Lab-Scale Investigation on Co-Digestion of Organic Wastes, Water Environment Federation—Joint Residuals and Biosolids Management Conference 2005 (Apr. 17, 2005) (USA).
Curtiss, *Bacterial Cell Wall*, Microbiology, W.W. Norton & Co. (1976).
Dentel et al., *Overview of Electrical Arc Conditioning of Biosolids* in Water Environment Research Foundation: Workshop #116 Recent Advances in Biosolids Research: Conditioning, Dewatering, and Beneficial Use 86-98 (1999) (USA).
Dossenbach et al., *Pulse Current Electrodeposition of Palladium Silver Alloys* in AESF (American Electroplaters and Surface Finishers Society) Third International Pulse Plating Symposium H1-H3 (1986) (USA).
El-Shazly et al., *High-Speed Metal Deposition Using Interrupted Current Techniques* in AESF (American Electroplaters and Surface Finishers Society) Third International Pulse Plating Symposium C1-C11 (1986) (USA).
Gaudy, et al., *The Microbiology of Waste Disposal*, in The Microbiology of Waste Waters, W.B. Saunders & Comp., chapter 36 (1971).
Graham Mfg. Co., *Heliflow Heat Exchanger*.
Gupta, R.P., *Pulsed High Electric Field Sterilization*.
Gutierrez, *Recent Advances in Pulse Plating Power Supply Technology & Plating Capability*, AESF 5th Pulse Plating Symposium 1-23 (Jun. 2000) (USA).
Kady International materials—4 pages (circa 1999) (USA).
Kady International materials—2 pages (circa 1999) (USA).
Koelzer, *Back to the Basics: Pulse Math*, Plating & Surface Finishing (Dec. 2000) (USA).
Liu et al., Electricity Generation Using an Air-Cathode Single Chamber Microbial Fuel Cell in the Presence and Absence of a Proton Exchange Membrane, Environmental Sci & Tech, 4040-4046 (Jun. 12, 2004) (USA).
Liu et al., Production of Electricity During Waste Water Treatment Using a Single Chamber Microbial Fuel Cell, Environmental Sci & Tech, 2281-2285 (Feb. 21, 2004) (USA).
Logan, Extracting Hydrogen and Electricity from Renewable Resources, Environmental Sci. & Tech, 160A-167A (May 1, 2004) (USA).
*Marlen OPTT Series Pump/Stuffer* product brochure.
Mertens et al., *Developments of Nonthermal Processes for Food Preservation*, Food Tech. 46(5):124, 126-133 (May 1992) (USA).
*Method Improves Sludge Digestion*, Waste Treatment Tech. News v.12 i8 (1996) (USA).
Milad et al., *PPR Plating for HDI*, PC Fab, 40, 42, 44, 46 (2000) (USA).
Minnesota Dairy Runs Hydrogen Fuel Cell on Biogas, Biocycle, 58 (Jun. 2005) (USA).
Morrisey et al., Sterilization Methods Used in Microbiology, *Sterilization Technology*, 1993.
Newmet-Thermet Krebsoge Company, *Porous Metal Products* products brochure.
Oh et al., Biological Hydrogen Production Using a Membrane Bioreactor, Biotechnology & Bioeng'g 119-127 (Jul. 5, 2004) (USA).
Parry et al., Bioenergy Conversion of Cow Manure, Water Environment Federation—Joint Residuals and Biosolids Management Conference 2005 (Apr. 17, 2005) (USA).
Peshkovsky et al., *Dipolar Interactions in Molecules Aligned by Strong AC Electric Fields*, J. Magnetic Resonance, 147:104-109 (2000) (USA).

Puippe, *Influence of Charge and Discharge of Electrical Double Layer in Pulse Plating* in Theory and Practice of Pulse Plating (America Electroplaters and Surface Finishers Society), ch. 4, pp. 41-43 (1986) (USA).

Puippe, *Qualitative Approach to Pulse Plating* in Theory and Practice of Pulse Plating (America Electroplaters and Surface Finishers Society), ch. 1, pp. 1-3 (1986) (USA).

Stafford et al., A Competitive Approach to Bioenergy Management, Water Environment Federation—Joint Residuals and Biosolids Management Conference 2005 (Apr. 17, 2005) (USA).

U.S. Departments of Energy and Agriculture, Biomass as Feedstock for a Bioenergy and Bioproducts Industry: The Technical Feasibility of a Billion-Ton Annual Supply (Apr. 2005) (USA) (misnumbering in original).

Water Environment Federation, Be in the Know . . . Go with the Flow! (Sep. 2001) (USA).

U.S. Food and Drug Administration, *Kinetics of Microbial Inactivation for Alternative Food Processing Technologies—Pulsed Electric Fields* (Jun. 2000) (USA).

Wadehra et al, *Reduced Wasting from Activated Sludge Processes Using a Mechanical Cell Lysis Technology* in WEFTEC 1999, (1999) (USA).

Zhang, Q. H., Monsalve-Gonzalez, A., Barbosa-Cánovas, G. V. and Swanson, B. G., *Inactivation of E. coli and S. cerevisiae by pulsed electric fields under controlled temperature conditions*, Transactions of the ASAE. 37(2):581-587 (1994) (USA).

Zhang, Q. H., Chang, F.-J. and Barbosa-Cánovas, G. V., *Inactivation of microorganisms in a semisolid model food using high voltage pulsed electric fields*, Lebensm Wiss Technol. 27(6):538-543 (1994) (believed to be Germany).

Zhang, Q. H., Qin, B.-L., Barbosa-Cánovas, G. V. and Swanson, B. G, *Inactivation of E. coli for food pasteurization by high-strength pulsed electric fields*, J. Food Process Preserv. 19(2):103-118 (1995) (USA).

Zhang, Q. H., Barbosa-Cánovas, G. V. and Swanson, B. G., *Engineering aspects of pulsed electric field pasteurization*, J. Food Eng. 25(2):261-281 (1995) (Great Britain).

Zhang, Q. H., Qiu, X. and Sharma, S. K., *Recent development in pulsed electric field processing*. National Food Processors Association—New Technologies Yearbook. 31-46 (1997) (believed to be USA).

Supplemental European Search Report, issued in regard to EP application No. 01924692 (3 pages, Feb. 29, 2008).

* cited by examiner

Schematic of Prokaryotic Cell

Schematic of Eukaryotic Cell

METHOD OF AND APPARATUS FOR CONVERTING BIOLOGICAL MATERIALS INTO ENERGY RESOURCES

This application claims the benefit of U.S. Provisional Patent Application No. 60/599,355, filed on Aug. 6, 2004, which application is incorporated herein by reference in its entirety. This application is also a continuation-in-part of U.S. application Ser. No. 10/795,944, filed Mar. 8, 2004, now U.S. Pat. No. 7,001,520, which is continuation of U.S. application Ser. No. 10/270,420, filed Oct. 15, 2002, now U.S. Pat. No. 6,709,594, which is continuation-in-part of U.S. application Ser. No. 10/107,614, filed Mar. 26, 2002, now U.S. Pat. No. 6,540,919, which is continuation of U.S. application Ser. No. 09/612,776, filed Jul. 10, 2000, now U.S. Pat. No. 6,395,176, which is continuation-in-part of U.S. application Ser. No. 09/468,427, filed on Dec. 21, 1999, abandoned, which is continuation of U.S. application Ser. No. 09/229,279, filed Jan. 13, 1999, now U.S. Pat. No. 6,030,538, which applications are hereby incorporated by reference in their entirety in the present application.

BACKGROUND

This patent is directed to a method and apparatus for converting biological materials into energy resources, and, in particular, to a method and apparatus using pulsed electric fields to release intracellular materials from biological materials in a method and apparatus for converting the biological materials into energy resources.

Significant energy potential exists in biological materials, including biological wastes such as municipal and industrial wastes. It has been estimated that the animal waste produced on an annual basis in the United States has an energy value equivalent to 21 billion gallons of gasoline. Elsewhere, researchers have stated that the organic content of human wastewaters produced in the United States has an annual energy value equivalent to 0.11 quadrillion BTUs, with an estimated annual monetary value of $2 billion. See Logan, Extracting Hydrogen and Electricity from Renewable Resources, Envtl. Sci. and Tech., vol. 41, pp. 161-167 (2004), hereby incorporated by reference in its entirety. Researchers have also stated that animal wastewaters produced in the United States have an annual energy potential equivalent to 0.3 quadrillion BTUs. See Logan, above. By comparison, the total annual electricity generation of the United States is only 13 quadrillion BTUs. It is further believed that significant energy potential exists in industrial wastes and wastewaters, including those produced by pulp and paper processing and by food processing.

Various technologies, including methanogenesis, biohydrogen production using fermentative processes, and direct electricity production using biofuel cells or microbial fuel cells, have been demonstrated to be capable of producing energy resources from wastes and wastewaters. However, the efficiencies of the energy generation using these technologies, both in terms of rate and net units generated, remain problematic. For example, while researchers have estimated that hydrogen production from wastewater has the greatest potential for economical production of biohydrogen from renewable resources, fermentative technologies used to produce hydrogen from wastewater have been found to capture only 15% of the available organic energy. See Logan, above. This represents less than half of the estimated conversion efficiency of 33%.

SUMMARY OF THE INVENTION

In one aspect, a method of converting biological material into energy resources includes transmitting biological material to a pulsed electric field station, and applying a pulsed electric field to the biological material within a treatment zone in the pulse electric field station to generate treated biological material. The method also includes transmitting the treated biological material to a biogenerator, and processing the treated biological material in the biogenerator to produce an energy resource.

In another aspect, a converter that converts biological material into energy resources includes a pulsed electric field station, the pulsed electric field station comprising an inlet adapted to receive biological material, a treatment chamber through which biological material received via the inlet passes and including at least two spaced electrodes between which is generated a pulsed electric field and which define at least one treatment zone therebetween, and an outlet adapted to pass treated biological material. The converter also includes a biogenerator, the biogenerator comprising an inlet coupled to the outlet of the pulsed electric field station, at least one chamber in which the treated biological material is processed into an energy resource, a first outlet adapted to pass the energy resource and a second outlet adapted to pass processed treated biological material.

In a further aspect, a wastewater treatment system including a primary treatment station that receives a wastewater stream and separates the wastewater stream into primary sludge and a first liquid fraction, a secondary treatment station coupled to the primary treatment station, the secondary treatment station receiving the first liquid fraction and digesting the solids in the liquid fraction to produce activated sludge and a second liquid fraction, and a bioreactor that receives the primary sludge and at least part of the activated sludge and digests the primary sludge and activated sludge to produce a digested product. The system also includes a converter which receives at least part of at least one of the wastewater stream, the primary sludge, the activated sludge, the first liquid fraction, the second liquid fraction and the digested product. The converter includes a pulsed electric field station, the pulsed electric field station comprising an inlet adapted to receive biological material, a treatment chamber through which biological material received via the inlet passes and including at least two spaced electrodes between which is generated a pulsed electric field and which define at least one treatment zone therebetween, and an outlet adapted to pass treated biological material. The converter also includes a biogenerator, the biogenerator comprising an inlet coupled to the outlet of the pulsed electric field station, at least one chamber in which the treated biological material is processed into an energy resource, a first outlet adapted to pass the energy resource and a second outlet adapted to pass processed treated biological material.

Additional aspects of the disclosure are defined by the claims of this patent.

DETAILED DESCRIPTION OF VARIOUS EMBODIMENTS

Although the following text sets forth a detailed description of numerous different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
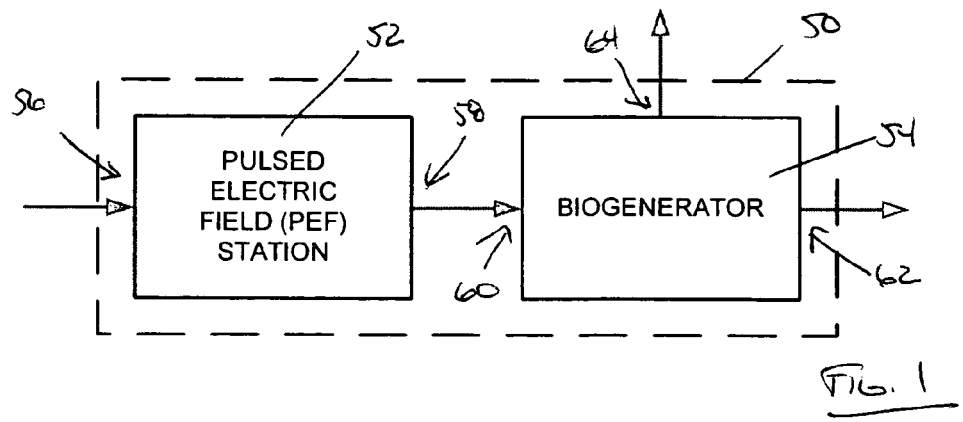
FIG. 1 is a schematic view of a converter according to the present disclosure.

FIG. 1 illustrates an embodiment of a converter 50 according to the present disclosure. The converter 50 may include a pulsed electric field (PEF) station 52 and a biogenerator 54. Biological materials may flow into the PEF station 52 via an inlet 56, may be treated, and may then be released via an outlet 58. The outlet 58 may be coupled to an inlet 60 of the biogenerator 54, permitting the treated biological materials to flow from the PEF station 52 into the biogenerator 54. After processing in the biogenerator 54, the processed, treated biological materials may pass from the biogenerator via a first outlet 62, while the energy resources generated by the biogenerator 54 may be extracted or harvested via a second outlet 64.

A wide variety of biological materials may be introduced into the converter 50 for conversion into an energy resource. For example, the biological materials may include, for example, organic waste materials, such as municipal wastewater and wastes, industrial wastewater and wastes (such as pulp and paper wastewater and wastes, brewing wastewater and wastes, and food processing wastewater and wastes), and agricultural wastewater and wastes (including animal products and by-products, such as manure, and plant wastes). Alternatively, the biological materials may include materials generated by or from waste treatment facilities, such as sludges (including primary and waste activated sludges), active microorganisms from bioreactors (including both the active microorganisms used to carry out digestion in the bioreactors and any excess microorganisms produced as a product of digestion) and effluents. As a further alternative, the biological materials need not be wastes, but may be materials that have value or alternative uses, but for which the decision has been made to convert the biological materials into energy resources instead of putting the biological materials to the alternative use.

Figure 2:
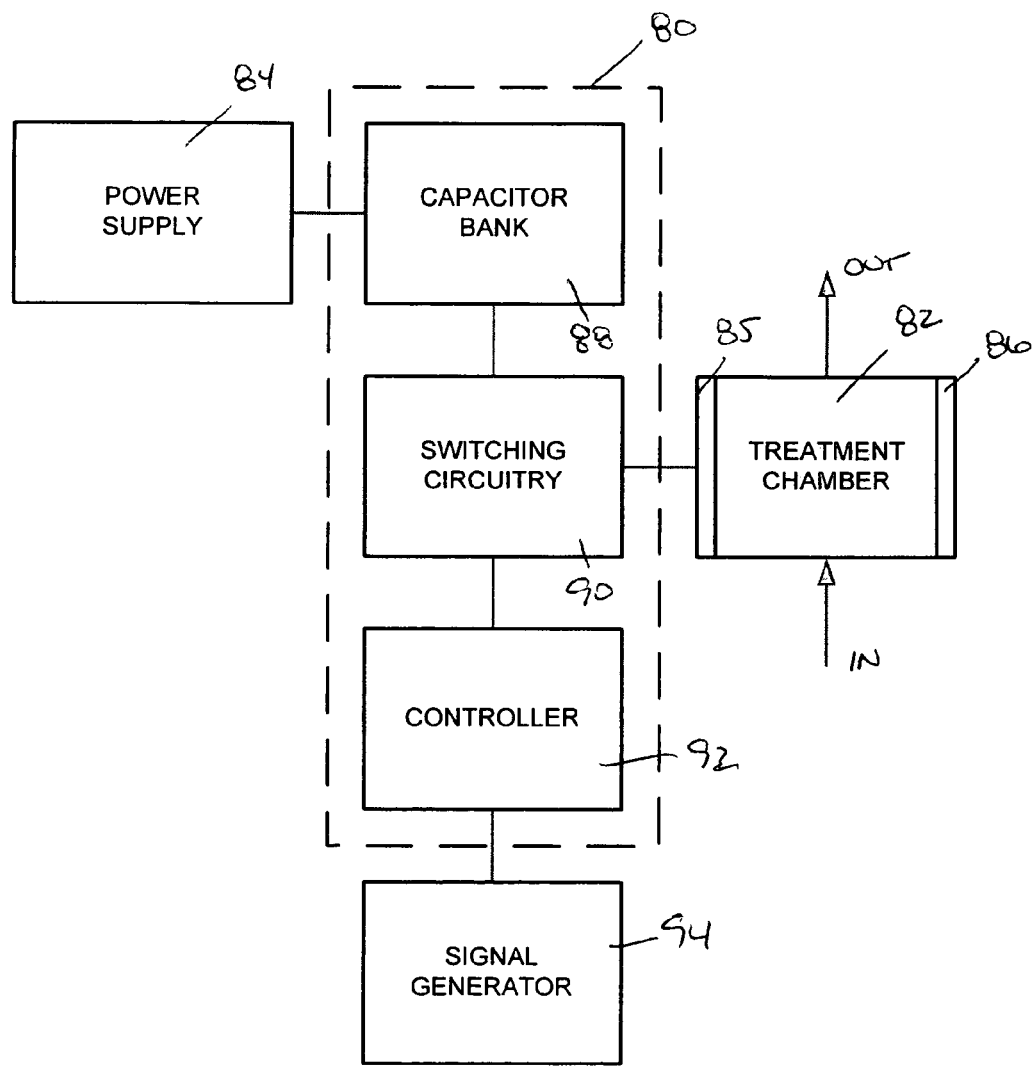
FIG. 2 is a schematic view of an embodiment of a pulsed electric field (PEF) station for use in the converter of FIG. 1.

An embodiment of the PEF station 52 is shown in greater detail in FIG. 2. The PEF station 52 may include a pulse generator 80 and a treatment, or PEF, chamber 82. In particular, materials contained in or passing through the treatment chamber 82 may be subjected to non-arcing electric field pulses generated by the pulse generator 80.

The electric field pulses may be generated by applying a voltage pulse to the electrodes, the pulse having a square-wave shape. However, the pulses may also have an exponentially decaying or oscillatory shape. Further, the pulses may be monopolar, bipolar, or even instant reverse charges. It is presently believed that the bipolar pulses may enhance the release of the cell contents, as is explained in greater detail below, and may improve energy utilization and electrode performance.

The electric field pulses may be of an individual duration of 2 to 15 microseconds with a peak field strength of 15 to 100 kV/cm. Preferably, the electric field pulses may be of an individual duration of 2 to 8 microseconds with a peak field strength of 20 to 60 kV/cm. The pulses may repeat at frequencies of between 2,000 and 10,000 pulses per second (or pps, and sometimes expressed in Hertz (Hz)). The resulting duration of treatment may be between 20 and 100 microseconds, which may be a function of the shape of the treatment zone (e.g., electrodes) and the characteristics of the electric field pulses.

Turning first to the pulse generator 80, the generator 80 may be coupled to a power supply 84, which the pulse generator 80 may use to generate a series of high voltage non-arcing electric field pulses across electrodes 85, 86 associated with the treatment chamber 82. Depending on the power supply 84 used, a voltage transformer may be included, coupled between the power supply 84 and the pulse generator 80. The pulse generator 80 may include a bank of capacitors 88 and switching circuitry 90 that may connect the bank of capacitors 88 across the electrodes 85, 86 to create the pulses within the treatment chamber 82. The switching circuitry 90 may be controlled by a controller 92 that has as an input a signal from a signal generator 94. By varying the characteristics of the signal from the signal generator 94, the characteristics of the pulses in the treatment chamber 82 may be varied.

The treatment chamber 82 may be similar or identical to those discussed in any of U.S. Pat. Nos. 5,695,650, 5,893,979, 6,030,538, 6,395,176, 6,491,820, 6,540,919, 6,709,594, each of which are incorporated herein by reference in their entirety.

Figure 3A:
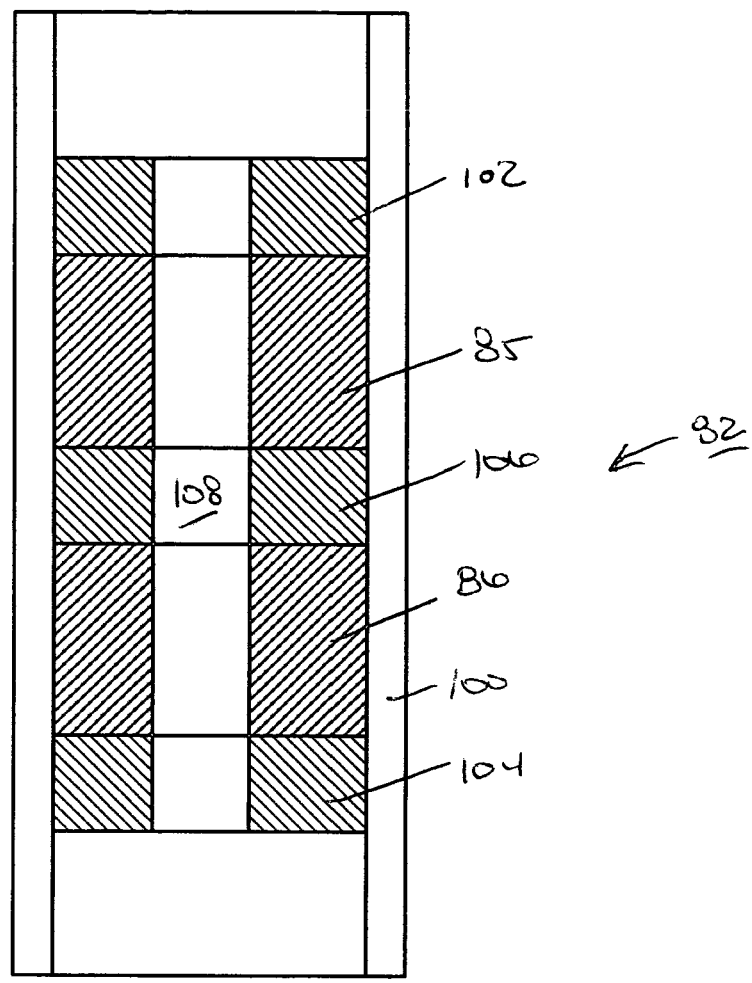
FIG. 3A is a cross-sectional view of an embodiment of a treatment chamber for use in the PEF station of FIG. 2.
Figure 3B:
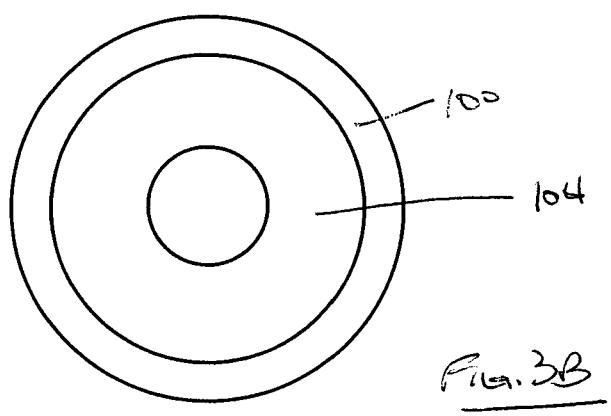
FIG. 3B is an end view of the treatment chamber of FIG. 3A.

Alternatively, an embodiment of the treatment chamber 82 is shown in FIGS. 3A and 3B. The treatment chamber 82 may include a housing 100, which in the present embodiment may be cylindrical in shape, as can be seen in FIG. 3B, although other geometries are possible. In the treatment chamber 82 may be disposed electrodes 85, 86, one of the electrodes 85, 86 coupled to a higher voltage and the other the electrodes 85, 86 coupled to ground or a lower voltage. Insulators 102, 104, 106 may be disposed at either side of the electrodes 85, 86 and between the electrodes 85, 86. The insulators 102, 104, as well as the housing 100, which may be made of an insulating material, isolate the electrodes 85, 86 from couplings which may be attached or secured to either end of the housing 100. Similarly, the insulator 106 and the housing 100 space the electrodes 85, 86 to define a treatment zone 108 disposed therebetween. In operation, the biological materials to be treated are passed through the treatment zone 108 as they pass through the treatment chamber 82.

Figure 4:
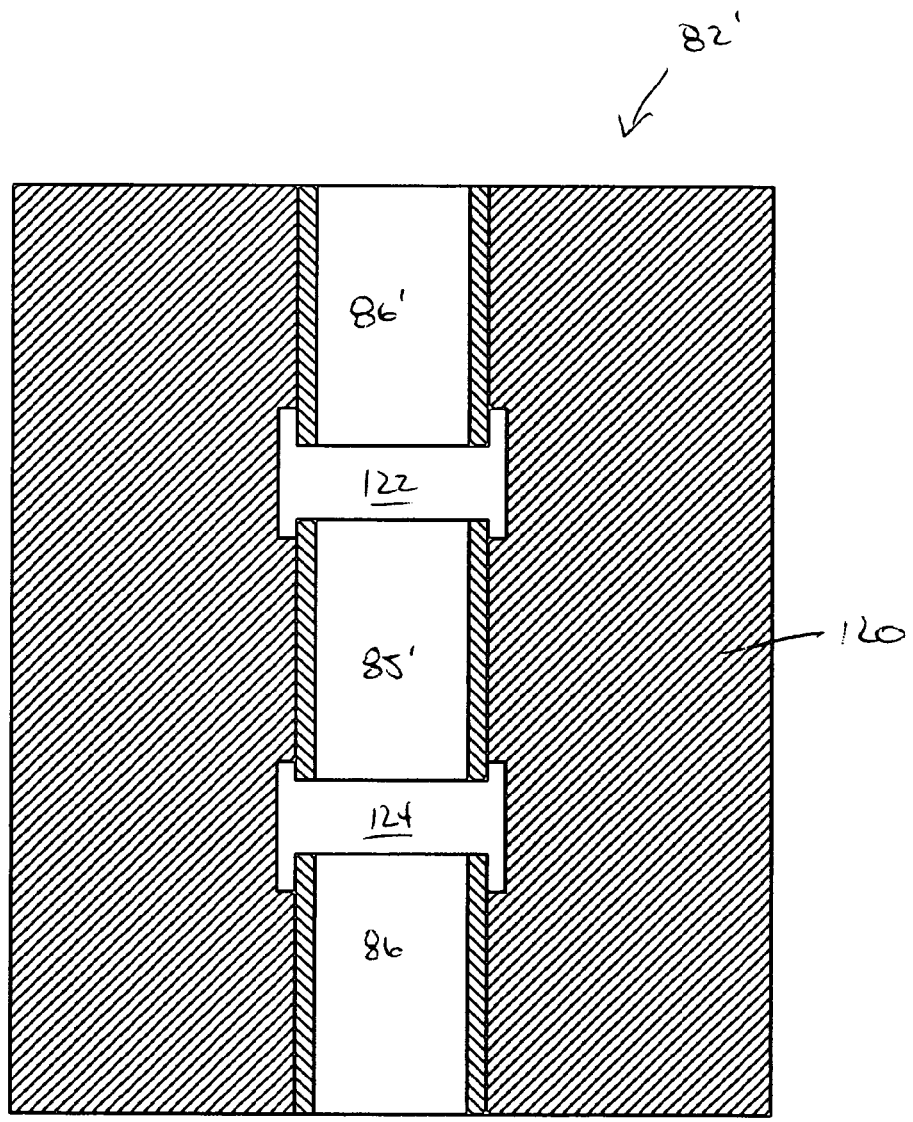
FIG. 4 is a cross-sectional view of another embodiment of a treatment chamber for use in the PEF station of FIG. 2.

As a further alternative, another embodiment of the treatment chamber 82, designated 82', is shown in FIG. 4. The treatment chamber 82' may include a supporting material 120, which may be made of a material having insulating properties. The supporting material 120 may also support three electrodes 85', 86', the electrode 85' being coupled to a higher voltage and the electrodes 86' being coupled to ground or a lower voltage. As shown, the electrodes 85', 86' may be cylindrical in shape, although other geometries are possible. According to this embodiment, two treatment zones 122, 124 are defined between the electrodes 85', 86'. In operation, the biological materials to be treated are passed through the treatment zones 122, 124 as they pass through the treatment chamber 82'.

It will be recognized that access to the substrate in biological materials is a significant threshhold that must be resolved if efficient generation of energy resources from biological materials using biological methods (for example, methanogenesis) is to be achieved. It is believed that treatment of the biological materials with PEF prior to processing in the biogenerator 54 may enhance the efficiency of the biogenerator, thereby removing a major obstacle to the commercialization of energy generation from biological materials, and in particular biological waste materials. To understand how PEF improves access to the substrate, a brief digression into cell structure and composition is appropriate.

Figure 11:
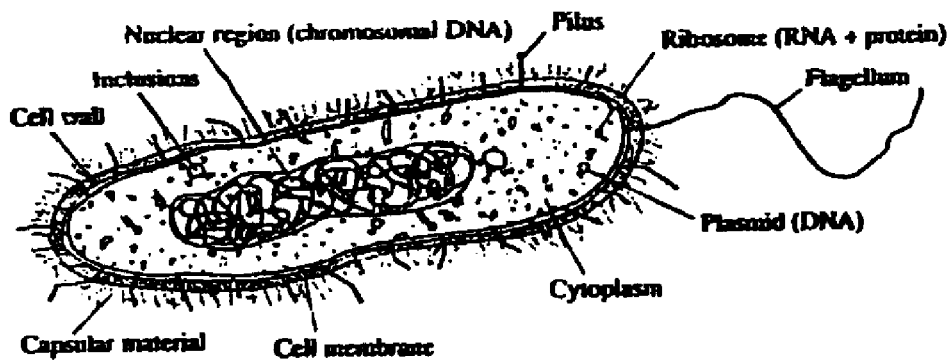
FIG. 11 is a schematic view of a prokaryotic cell.
Figure 12:
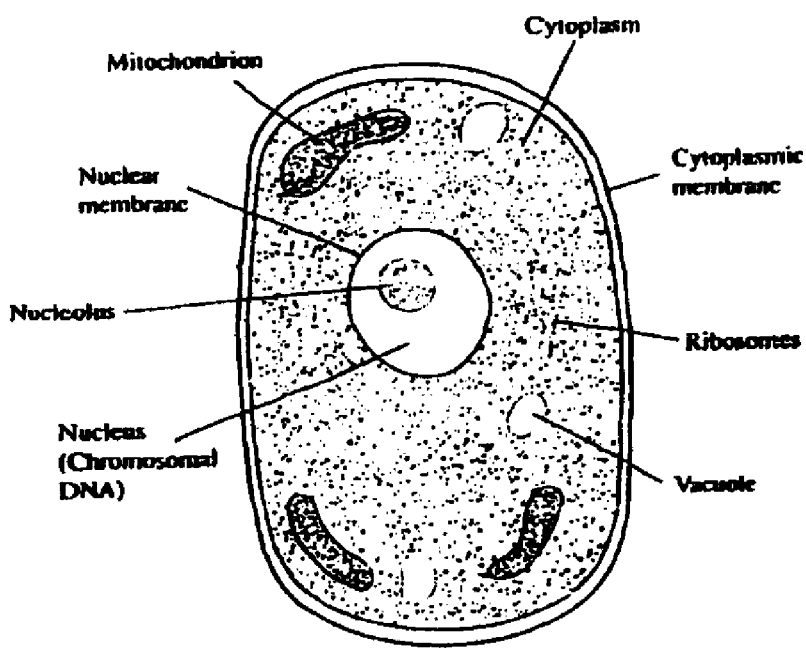
FIG. 12 is a schematic view of an eukaryotic cell.

A significant source of biological material, especially in wastes and wastewaters, is bacteria. Although not all bacteria have the same cell structure (compare the prokaryotic and eukaryotic microorganisms of FIGS. 11 and 12), most bacteria share certain common structural elements. Generally, bacteria may include a colloidal fluid, referred to as cytoplasm. It is in the cytoplasm that the dissolved nutrients, enzymes, other proteins, nucleic acids and other intracellular materials used in the energy generating reactions discussed below may be found. The cytoplasm may include both organic and inorganic biosolids. Further discussion of the composition of the cell, and in particular, the cytoplasm, can be found in Rittmann et al., Environmental Biotechnology (2d ed. 2001), which is hereby incorporated by reference in its entirety. However, bacteria may also include a cell wall and a cell membrane, which lies just beneath the cell wall, that surround the cytoplasm and limit access to the cytoplasm. Consequently, to obtain access to the cytoplasm, one must first deal with the cell wall and membrane.

One way in which access to the cytoplasm may be achieved is by digesting the cell wall and the cell membrane. Unfortunately, digestion is a slow and typically incomplete process. For example, it may take up to 40 days to achieve even incomplete digestion in anaerobic processing of wastewater by methanogenesis. In a similar vein, researchers have shown that with a given microbial fuel cell, electricity generation is almost immediate when using an easily accessible material, such as a solution of glucose and water, while electricity generation requires approximately 80 hours when wastewater is used. See Liu et al., Electricity Generation Using an Air-Cathode Single Chamber Microbial Fuel Cell in the Presence and Absence of a Proton Exchange Membrane, Envtl. Sci. and Tech., vol. 38, pp. 4040-4046 (2004), hereby incorporated by reference in its entirety.

The use of PEF treatment prior to processing in the biogenerator 54 looks to overcome the cell wall/membrane obstacle. It is believed that when a voltage gradient of one volt or greater is impressed over a microorganisms cell structure, the structure experiences a change referred to as electroporation. More particularly, in electroporation, it is believed that the high voltage electric field pulses temporarily destabilize the lipid bilayer and proteins of the cell membrane. As a consequence of this destabilization, it is believed that the cell membrane experiences an increase in permeablity. As additional material flows into the cell, because of the increased permeability, it is further believed that the cell swells and the cell wall and membrane eventually rupture. With the cell wall and membrane ruptured, the contents of the cell may be released, which may make the cell contents available as a substrate for energy resource generating reactions in the biogenerator 54.

Testing of PEF treatment on biowaste has been conducted, and the following results have been observed. In regard to the pulsed electric field used, the pulses had a field strength of 17.3 to 20.5 kV/cm, a pulse width of 4 to 6 microseconds, and a frequency of 2000 to 2500 pps. The treatment chamber was similar to that shown in FIGS. 3A and 3B, with the electrodes shaped such that the treatment zone provided a treatment duration of 20 to 100 microseconds. The testing was conducted over a total period of approximately 500 hours. Samples were collected on a daily basis, and analyzed to determine the release of soluble organic and inorganic material from cells relative to the starting materials. A summary of the test results showing the change in soluble material following PEF treatment is shown in Table 1.

TABLE 1

Release of Soluble Cellular Contents

| Parameter Measured | Average Percentage Increase |
| --- | --- |
| Total dissolved solids | 10.8% |
| Total organic carbon | 72.8% |
| Soluble chemical oxygen | 35% |
| Soluble ammonia nitrogen | 29.7% |
| Soluble orthophosphate | 15.4% |
| Soluble total phosphorus | 65% |
| Total kjeldahl nitrogen | 34.3% |

It is submitted that the data in Table 1 indicates that the cell walls and membranes are sufficiently perforated as a consequence of the PEF treatment, leading to the observed increases in the release of the water-soluble cell contents of the treated biowastes. It is further believed the increased amount of soluble organic material is released and available for more efficient consumption and conversion into energy resources.

As stated above, the treated biological material may pass from the PEF station 52 to the biogenerator 54 via the PEF outlet 58 and the biogenerator inlet 60. While the PEF outlet 58 is shown coupled directly to the biogenerator inlet 60 in FIG. 1 such that all of the treated biological material flows into the biogenerator 52, other alternatives are possible. For example, a fraction of the treated biological material may be diverted before entry into the biogenerator. This fraction of the treated biological material may then flow into the inlet 56 of the PEF station 50 for further treatment. Alternatively, the fraction may be diverted to a bioreactor for digestion before being reintroduced into the PEF station 52 or passed to the biogenerator 54.

Figure 7:
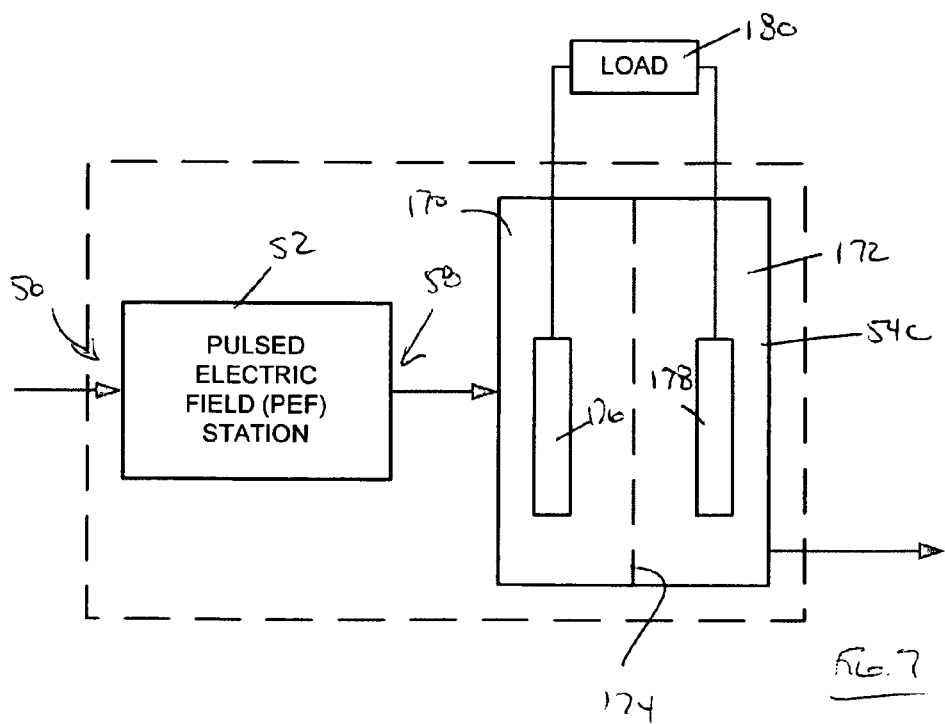
FIG. 7 is a schematic view of a third embodiment of the converter of FIG. 1, the generator being a two-chamber microbial fuel cell.
Figure 8:
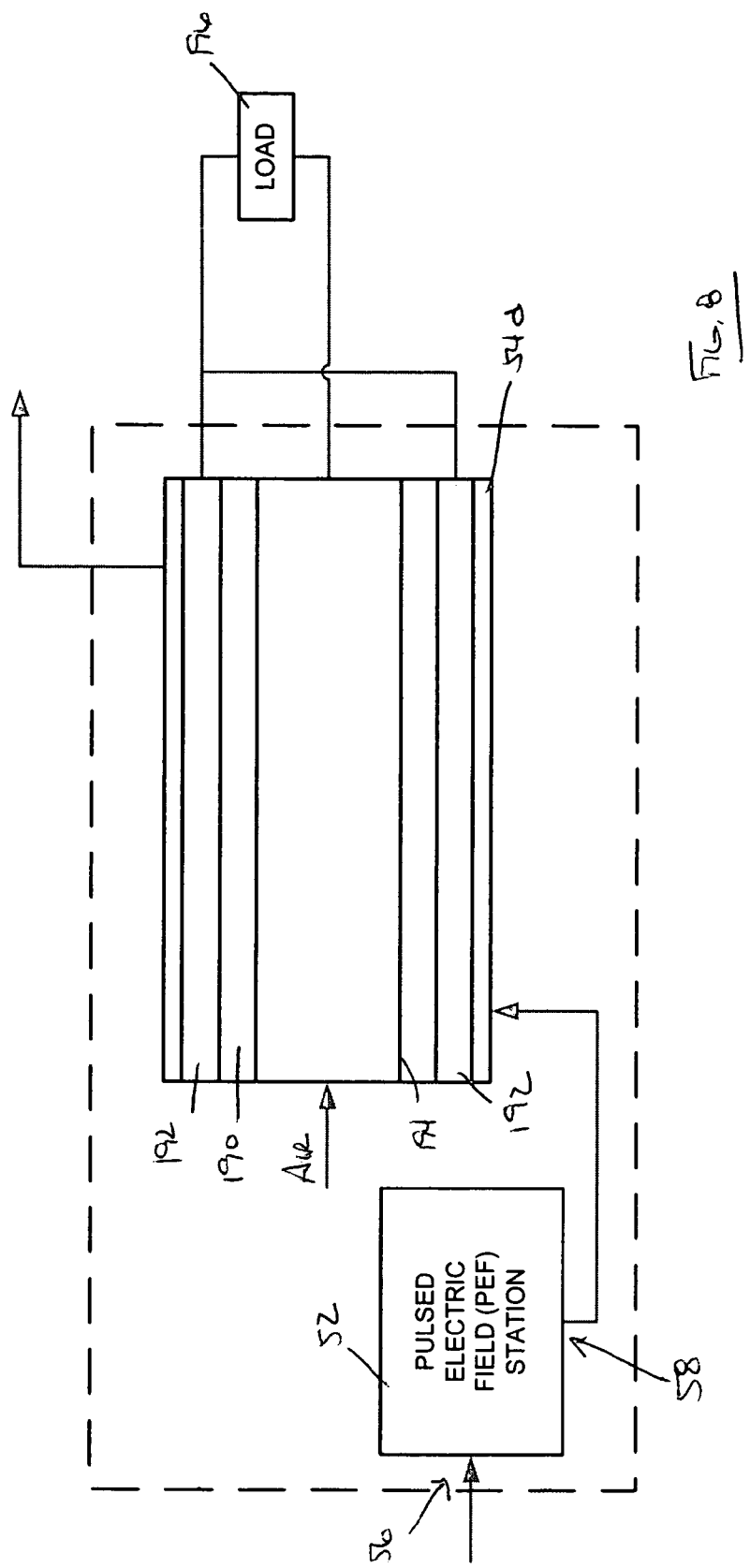
FIG. 8 is a schematic view of a fourth embodiment of the converter of FIG. 1, the generator being a single chamber microbial fuel cell.

A variety of biogenerators 54 may be used with the PEF station 52. Four embodiments of a biogenerator 54 are shown in FIGS. 5-8. However, it will be recognized that still further embodiments of biogenerator may be used with and may benefit from use with the PEF station 52. The embodiments of the biogenerator 54 shown in FIGS. 5-8 may generate energy resources in the form of fuels, such as methane and/or hydrogen, or electricity. Moreover, where the energy resource generated is a fuel, the fuel may be combusted in an engine, which in turn may be coupled to a conventional generator to convert the kinetic energy into electricity. The embodiments of the biogenerator 54 may include generators 54a, 54b that use methanogenesis (FIG. 5) and two-stage methane and hydrogen generation (FIG. 6) as well as one- and two-chamber microbial fuel cells 54c, 54d (FIGS. 7 and 8).

Figure 5:
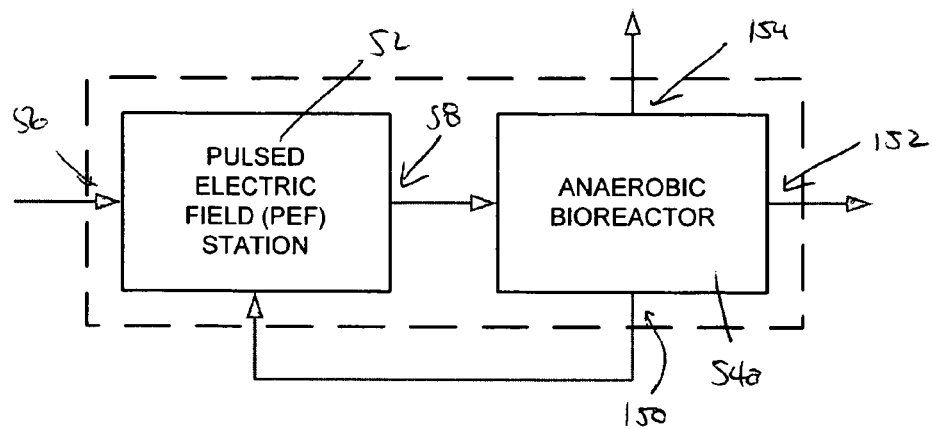
FIG. 5 is a schematic view of a first embodiment of the converter of FIG. 1, the generator using methanogenesis.

As shown in FIG. 5, biological materials may enter the PEF station 52 via the inlet 56, may be treated, and may pass to the biogenerator 54a via outlet 58 and inlet 60. The biogenerator 54a according to this embodiment may be an anaerobic bioreactor that generates methane gas from treated biological materials by methanogenesis. It will be recognized that methanogenesis is an anaerobic process in which electron equivalents in the organic matter are used to reduce carbon to its most reduced oxidation state, $CH_4$, or methane. See generally, Logan, Extracting Hydrogen and Electricity from Renewable Resources, Envtl. Sci. and Tech., vol. 41, pp. 161-167 (2004), hereby incorporated by reference in its entirety. As an initial step, bacteria may hydrolyze complex organic matter, such as carbohydrates, proteins and fats, into simple carbohydrates, amino acids, and fatty acids. Other bacteria may then use hydrogen as an electron donor and carbon dioxide as an electron acceptor to generate methane gas. One of the byproducts of the methanogenesis process may be water.

As shown, there may be three outlets 150, 152, 154 from the biogenerator 54a. The first outlet 150 may be used to pass some of the solids materials from the biogenerator 54a to the PEF station 52 for further processing along with the biological materials entering the PEF station 52 via the inlet 56. The processed, treated biological materials from the biogenerator 54a may be mixed with the biological materials from the inlet 56 before entry into the PEF station 52 or within the treatment chamber 82 of the PEF station 52, or may be processed in parallel with the materials biological materials entering via the inlet 56. The second outlet 152 may be used to pass a liquid fraction (primarily water) released from the processed, treated biological materials as a consequence of the PEF treatment and as a consequence of the methanogenesis process. The third outlet 154 may be used to pass the gaseous methane generated by the biogenerator 54a.

Figure 6:
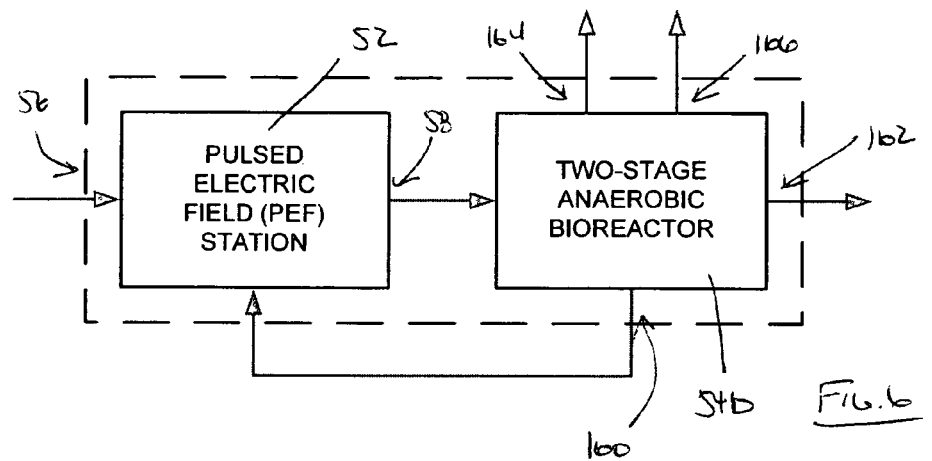
FIG. 6 is a schematic view of a second embodiment of the converter of FIG. 1, the generator using fermentive processes to produce hydrogen and methane.

As shown in FIG. 6, biological materials may enter the PEF station 52 via the inlet 56, may be treated, and may pass to the biogenerator 54b via outlet 58 and inlet 60. The biogenerator 54b according to this embodiment may include two-stage anaerobic bioreactor that generates methane gas and hydrogen gas from treated biological materials by biohydrogen. In the first stage, hydrogen may be recovered during hydrolysis and fermentation of the biological material. In the second stage, the remaining biological material would be processed using methanogenesis or a similar process.

As shown, there may be four outlets 160, 162, 164, 166 from the biogenerator 54b. The first outlet 160 may be used to pass some of the solids materials from the biogenerator 54b to the PEF station 52 for further processing along with the biological materials entering the PEF station 52 via the inlet 56. The processed, treated biological materials from the biogenerator 52b may be mixed with the biological materials from the inlet 56 before entry into the PEF station 52 or within the treatment chamber 82 of the PEF station 52, or may be processed in parallel with the materials biological materials entering via the inlet 56. The second outlet 164 may be used to pass a liquid fraction (primarily water) released from the processed, treated biological materials. The third outlet 164 may be used to pass the gaseous methane generated by the biogenerator 54b, while the fourth outlet 166 may be used to pass the gaseous hydrogen generated by the biogenerator 54b.

As shown in FIG. 7, biological materials may enter the PEF station 52 via the inlet 56, may be treated, and may pass to the biogenerator 54c via outlet 58 and inlet 60. The biogenerator 54c according to this embodiment includes two-chamber microbial fuel cell that generates electricity from biological materials, such as is described in U.S. Pat. No. 5,976,719, which is incorporated by reference in its entirety. In particular, the biogenerator 54c may include a first chamber 170 that is substantially oxygen-free and a second chamber 172 that is oxygen-rich. The two chambers 170, 172 may be separated by a proton exchange membrane 174. Microorganisms capable of digesting biological materials, such as the treated biological materials from the PEF station 52, may be disposed in the first chamber 170. These microorganisms may attach to an anode 176 disposed in the first chamber 170, may oxidize the treated biological material entering the first chamber 170, and may transfer electrons to the anode 176. The released electrons may travel from the anode 176 to a cathode 178. The electricity generated by the movement of the electrons from anode 176 to cathode 178 may be used by a load 180 disposed between the anode 176 and the cathode 178. Alternatives are described in Liu et al., Electricity Generation Using an Air-Cathode Single Chamber Microbial Fuel Cell in the Presence and Absence of a Proton Exchange Membrane, Envtl. Sci. and Tech., vol. 38, pp. 4040-4046 (2004), hereby incorporated by reference in its entirety.

As shown in FIG. 8, biological materials may enter the PEF station 52 via the inlet 56, may be treated, and may pass to the biogenerator 54d via outlet 58 and inlet 60. The biogenerator 54d according to this embodiment may includes a single-chamber microbial fuel cell that generates electricity from biological materials, such as is described in Liu et al., Electricity Generation Using an Air-Cathode Single Chamber Microbial Fuel Cell in the Presence and Absence of a Proton Exchange Membrane, Envtl. Sci. and Tech., vol. 38, pp. 4040-4046 (2004), hereby incorporated by reference in its entirety. In particular, the biogenerator 54d may include a chamber 190. Microorganisms capable of digesting biological materials, such as the treated biological materials from the PEF station 50, may be disposed on a plurality of anodes 192 arranged in a cylindrical geometry. An air-porous cathode 194 may be disposed centrally relative to the anodes 194, and an air stream may be passed therethrough. As for alternatively embodiments of this biogenerator, see Liu et al., Electricity Generation Using an Air-Cathode Single Chamber Microbial Fuel Cell in the Presence and Absence of a Proton Exchange Membrane, Envtl. Sci. and Tech., vol. 38, pp. 4040-4046 (2004), hereby incorporated by reference in its entirety.

Figure 9:
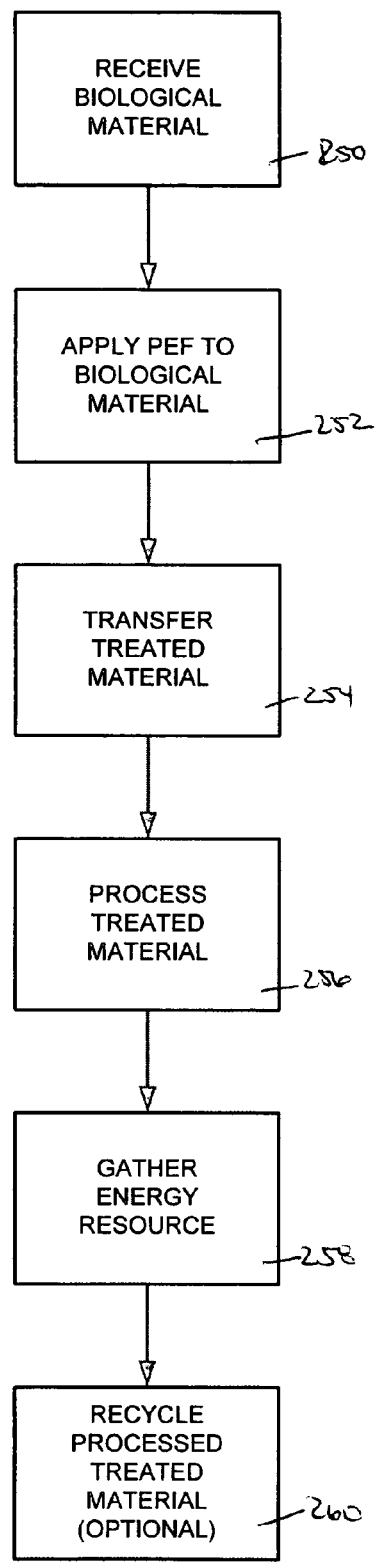
FIG. 9 is a block diagram of a method of converting biological materials into energy resources according to the present disclosure.

Having thus explained the structure of the converter 50, the process of converting biological materials to energy resources is now discussed with reference to FIG. 9. Starting at block 250, the biological materials may be received at the PEF station 52. Pulsed electric fields may then be applied to the biological materials at block 252, and the treated biological materials may be transferred to the biogenerator 54 at block 254. The treated materials may be processed at the biogenerator 54 at block 256, and the energy resources generated by the processing of the treated biological materials may be gathered at block 258. As shown above, some but not all of the embodiments of the converter 50 may have recycling of at least a fraction of the processed, treated biological materials. In those embodiments of the converter 50 that include recycling, the processed, treated biological materials may be recycled at block 260.

Having thus discussed the structure and operation of the converter 50, an embodiment of a system wherein one or more of the converters 50 may be used is now discussed.

Figure 10:
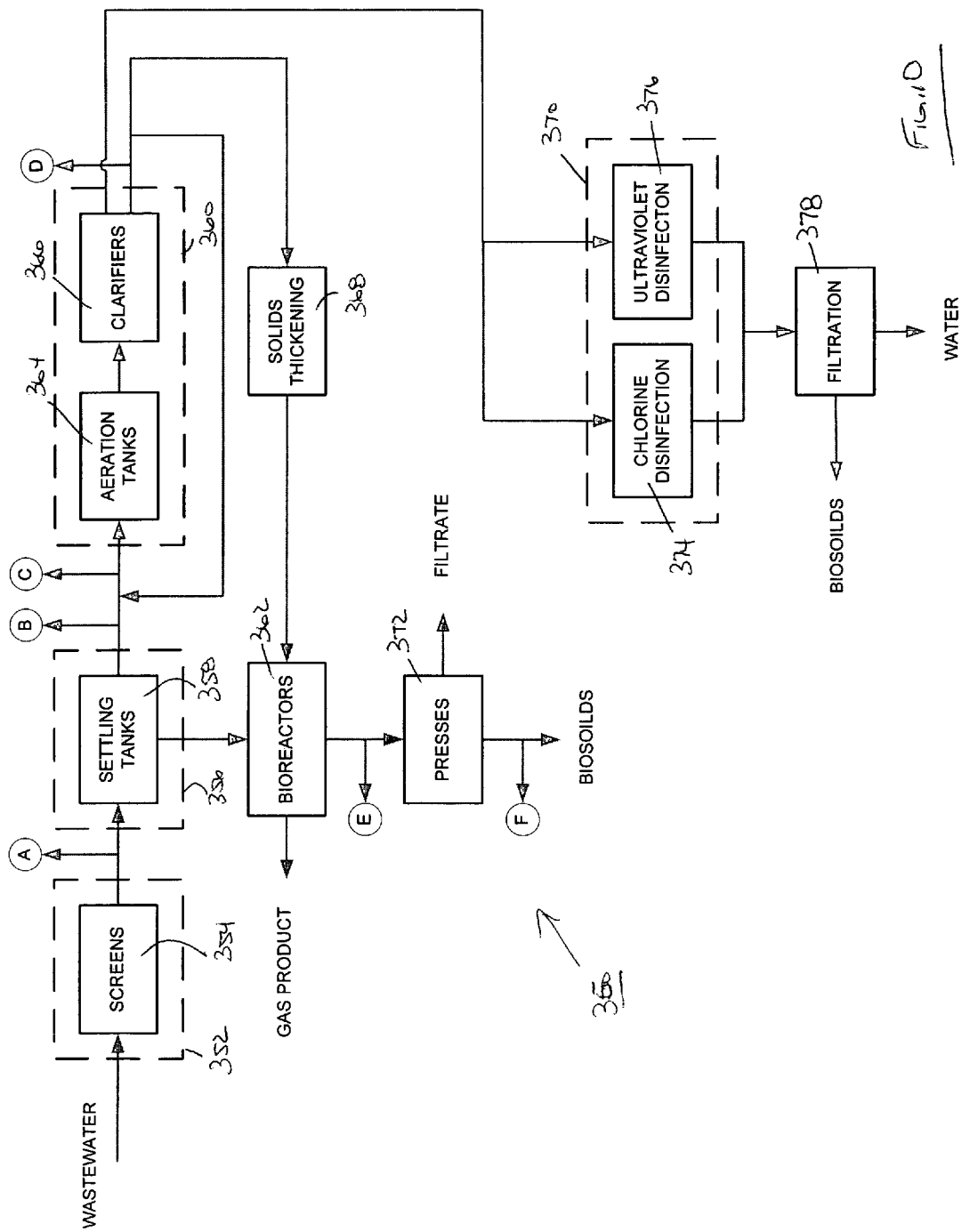
FIG. 10 is a schematic view of a wastewater treatment system in which the converter according to FIG. 1 may be used, exemplar positions for integration of the converter into the system being marked.

One example of a system in which one or more of the converters 50 according to the present disclosure may be used is a wastewater treatment system, such as is shown in FIG. 10. The wastewater treatment methods in use today have changed little in their basic principles since they were first developed in the early 1900's. Simply stated, microorganisms are used to consume and to oxidize the organic wastes present in wastewater so that the resultant effluent may be discharged into a large body of water, such as a river, lake or ocean. As a consequence, there are a variety of biological materials (wasterwater, sludges, microorganisms used by the bioreactors, and effluents, for example) present in such a system that may be converted by the converter 50 in energy resources. Furthermore, there is a large volume of this biological material available; over 33 billion gallons of domestic wastewater are treated each day in the United States.

As shown in FIG. 10, wastewater may enter the wastewater treatment system 350 at the upper left. The wastewater may flow first into a preliminary treatment station 352. The preliminary treatment station 352 may include one or more screens 354, which may be large metal grates that prevent larger objects in the wastewater stream from passing further downstream. After the wastewater stream passes through the preliminary treatment station 352, the wastewater stream may enter the primary treatment station 356.

The primary treatment station 356, according to this embodiment of the system 350, may include a plurality of settling tanks 358. According to other embodiments, the primary treatment station 356 may include a lagoon. The wastewater may be held in the primary treatment station 356 to permit larger solids, which were not removed in the preliminary treatment station 352, to separate from the remainder of the wastewater. The wastewater may also be held in the primary treatment station to permit lighter materials, such as oil and grease, to separate from the wastewater and float to the top of the tanks 358. The liquid fraction (which may still contain up to 5% biosolids, and may be referred to as primary effluent) may then be directed to the secondary treatment station 360, while the biosolids that settled to the bottom or floated to the top of the tanks 358 may be directed to one or more bioreactors 362. The materials that are directed to the bioreactors 362 may be referred to as primary treatment biosolids or primary sludge.

Leaving discussion of the bioreactors 362 for the moment, the secondary treatment station 360 may include one or more treatment substations. As shown, the secondary treatment station 360 may include a plurality of aeration tanks 364, which may also be referred to as bioreactors, and a plurality of clarifiers 366. Alternatively, the bioreactors used in the secondary treatment station may be facultative (able to function with or without oxygen), anoxic (low concentrations of oxygen) or anaerobic (without oxygen). According to the embodiment shown, the materials received from the primary treatment station 356 may be held in the aeration tanks 364 to permit microorganisms within the liquid fraction digest at least some of the biosolids remaining in an oxygen-rich environment. The biosolids and microorganisms may then be separated from the liquid fraction by the clarifiers 366. The fraction of the wastewater leaving the secondary treatment station 360 and containing a higher percentage of biosolids may be referred to as activated sludge. The fraction of the wastewater leaving the secondary treatment station 360 and containing a lower percentage of biosolids may be referred to as secondary effluent.

Some of the waste activated sludge, referred to as return activated sludge, may be returned to the secondary treatment station 360. The remainder of the activated sludge, referred to as waste activated sludge, may be passed along to the thickeners 368, where chemicals, such as polymers, are added to the waste activated sludge or gravity is used to increase the solids concentration. The thickened waste activated sludge may be passed along to the bioreactors 362.

The thickened waste activated sludge and the biosolids from the primary treatment station 352 may be mixed in the bioreactor(s) 362. In the bioreactors 362, the primary sludge and waste activated sludge may be exposed to microorganisms for anaerobic digestion. At least two product streams may exit the bioreactor 362: a first stream of gaseous byproducts, which may represent energy resources and may be gathered, and a second stream of solids, digested solids, microbiological processors, and liquid fraction, which is passed along to the presses 372.

In the presses 372, the biosolids exiting the bioreactor(s) 362 may be subjected to pressure to further separate liquids from the biosolids. For example, belt presses and/or centrifuges may be used. The remaining biosolids may be gathered from the presses 372 for disposal, in a landfill, for example, while the liquid fraction may be returned to secondary treatment station 360.

The secondary effluent passes to a final treatment station 370. The final treatment station 370 may include one or more substations, similar to the secondary treatment station 360. For example, the final treatment station may include a chlorine disinfection station 374 and an ultraviolet disinfection station 376. These stations may be concurrent or consecutive. The resultant flow may then be directed to the filtration station 378.

The filtration station 378 is an optional station, and may be included or omitted depending upon the use for which the resultant treated water is intended. One or more filters, such as sand or crushed coal filters, may be used to remove impurities remaining in the treated water stream. Biosolids collected on the filters may be removed, by backwashing the filters, for example, and directed to the bioreactors 362. The resulting water stream may be discharged into a river, lake or ocean, or put to an alternative use, such as for irrigation or for industrial processes.

The converter 50 according to the present disclosure may be used at any of a number of different places within the treatment system 350 just described. For ease of illustration, several junctions within the system 350 have been labeled, A through F. A converter 50 may receive part or all of the stream at these junctions. For example, a converter 50 may receive a fraction of the wastewater stream passing through junction A before it passes to the primary treatment station 356. Alternatively, a converter 50 may receive the stream from the primary treatment station 356 before it is combined with the return activated sludge (junction B), or after it is combined with the return activated sludge (junction C). As a further alternative, a converter 50 may receive activated sludge after the secondary treatment (junction D). As yet additional alternatives, a converter may receive the product of the bioreactors 362 (junction E) or the presses 372 (junction F).

As still further alternatives, more than one converter 50 may be used at any one junction, or at more than one junction (junctions B and D, for example). Moreover, a converter 50 may receive streams from more than one junction (junctions B and D, for example), which streams may be mixed prior to being introduced into the converter 50 (such as at junction C) or within the treatment chamber 82 of the PEF station 52 of the converter 50. Moreover, a stream from one of the junctions may be passed to a first converter 50, the product of which is then fed to a second converter 50. Still other alternatives will be recognized by one skilled in the art.

What is claimed is:

1. A method of converting municipal waste-water sludge, animal wastes or plant wastes into a gas product, the method comprising:

transmitting municipal waste-water sludge, animal wastes or plant wastes to a pulsed electric field station;

applying a pulsed electric field with a nonarcing voltage and pulse width to the municipal waste-water sludge, animal wastes or plant wastes within a treatment zone in the pulsed electric field station to generate treated municipal waste-water sludge, animal wastes or plant wastes, the pulsed electric field having pulses with a pulse width of 2 to 8 microseconds, a peak field strength of 20 to 60 kV/cm and a frequency of 2000 to 10000 pps;

transmitting the treated municipal waste-water sludge, animal wastes or plant wastes to a digester;

processing the treated municipal waste-water sludge, animal wastes or plant wastes in the digester to produce a gas product.

2. The method according to claim 1, comprising:

applying a voltage across first and second electrodes to generate the pulsed electrical field, the first and second electrodes defining a treatment zone therebetween.

3. The method according to claim 1, comprising:

applying a voltage across first and second electrodes and first and third electrodes to generate a first treatment zone between the first and second electrodes and a second treatment zone between the second and third electrodes.

4. The method according to claim 1, wherein a duration of treatment is a function of the shape of the treatment zone and the pulse width and frequency of the pulsed electric field, and the duration of treatment is between 20-100 microseconds.

5. The method according to claim 1, comprising:

transmitting municipal waste-water sludge, animal wastes or plant wastes, the municipal waste-water sludge, animal wastes or plant wastes being waste material gathered from one or more of municipal sources, industrial sources, and agricultural sources, to a pulsed electric field station.

6. The method according to claim 1, comprising:

transmitting the treated municipal waste-water sludge, animal wastes or plant wastes to an anaerobic digester;

processing the treated municipal waste-water sludge, animal wastes or plant wastes in the anaerobic digester to produce a gas product.

* * * * *